(12) United States Patent
Barth et al.

(10) Patent No.: US 7,347,921 B2
(45) Date of Patent: Mar. 25, 2008

(54) APPARATUS AND METHOD FOR THREADING A BIOPOLYMER THROUGH A NANOPORE

(75) Inventors: Phillip W. Barth, Portola Valley, CA (US); Carl A. Myerholtz, Cupertino, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 980 days.

(21) Appl. No.: 10/622,367

(22) Filed: Jul. 17, 2003

(65) Prior Publication Data
US 2005/0014162 A1    Jan. 20, 2005

(51) Int. Cl.
*G01N 27/447* (2006.01)
*G01N 27/453* (2006.01)

(52) U.S. Cl. ............... 204/451; 204/600; 204/601; 204/450

(58) Field of Classification Search ........ 204/450–455, 204/600–605
See application file for complete search history.

(56) References Cited

U.S. PATENT DOCUMENTS

| | | | |
|---|---|---|---|
| 6,344,316 B1 * | 2/2002 | Lockhart et al. ............... | 435/6 |
| 6,428,959 B1 * | 8/2002 | Deamer ........................... | 435/6 |
| 6,770,182 B1 * | 8/2004 | Griffiths et al. ................ | 204/453 |
| 6,806,543 B2 * | 10/2004 | Yamakawa et al. ........... | 257/414 |
| 7,005,264 B2 * | 2/2006 | Su et al. ......................... | 435/6 |
| 7,220,345 B2 * | 5/2007 | Bohn et al. ..................... | 204/600 |

FOREIGN PATENT DOCUMENTS

| WO | WO 01/81896 | 1/2001 |
|---|---|---|
| WO | WO 01/81908 | 1/2001 |

OTHER PUBLICATIONS

Sebastin et al. ("Kramers problem for a polymer in a double well," Physical Review E, vol. 62, No. 1, pp. 927-939, Jul. 2000).*
Han et al. ("Entropic trapping and Escape of Long DNA Molecules at Sibmicron Size Constriction," Physical Review of Letters, vol. 83, No. 8, Aug. 23 199, pp. 1688-1689.*
Siao ("Microfluidic: New Channels for Biological Research," Harvard Science Review, fall 2006, pp. 46-49).*
Jiali Li et al., "Ion-Beam Sculpting at Nanometre Length Scales", Nature, vol. 412, pp. 166-169, 2001.
John J. Kasianowicz et al., "Characterization of Individual Polynucleotide Molecules Using a Membrane Channel", Proc. Natl. Acad. Sci. USA, vol. 93, pp. 13770-13773, 1996.

* cited by examiner

*Primary Examiner*—Alex Noguerola

(57) ABSTRACT

The present invention provides an apparatus and method for threading a biopolymer through a nanopore. The apparatus of the present invention provides a substrate having a channel with a channel wall and a nanopore in the channel wall. The channel and nanopore are designed for receiving a biopolymer. The apparatus includes at least one set of electrodes for moving the biopolymer in a first direction past the nanopore, and at least one set of electrodes for moving the biopolymer through the nanopore in a second direction.

The invention also provides a method for threading a biopolymer through a nanopore. The method includes moving the biopolymer past the nanopore in a first direction, and threading the biopolymer through the nanopore in a second direction.

21 Claims, 8 Drawing Sheets

APPARATUS AND METHOD FOR THREADING A BIOPOLYMER THROUGH A NANOPORE

TECHNICAL FIELD

The invention relates generally to the field of biopolymers and more particularly to an apparatus and method for threading a biopolymer through a nanopore structure.

BACKGROUND

Manipulating matter at the nanometer scale is important for many electronic, chemical and biological advances (See Li et al., "Ion beam sculpting at nanometer length scales", Nature, 412: 166-169, 2001). A number of sequencing techniques have been proposed at the micrometer and nanometer scale in response to the human genome project. These techniques have been largely developed to help characterize and understand expression of genes in vivo. A popular technique uses micro arrays and hybridization of cDNA to determine the presence or absence of a particular target gene. A target gene and probe are exposed in solution and bind if relative hybridization sequences match. Hybridization is indicative of the presence of the sequence or target gene. A dye may be employed with the target or probe to then determine existence and efficiency of hybridizations. The technique has been extended for use in determining the presence of single nucleotide polymorphism (SNP'S) in target cDNA. Micro arrays provide the promise of being able to accurately and concurrently screen for a variety of diseases in a particular patient. A few major drawbacks of the micro array technique concerns difficulty in manufacturing as well as the long time for effective hybridizations between probe and target (generally overnight to maintain high specificity). In addition, the large amounts of genomic DNA in a patient would require an inordinate amount of time and work to sequence. Therefore, new techniques are now being explored to more quickly sequence biopolymers. Systems that are on the nanoscale are both effective on resources (limited materials), but also may more closely mimic the high speed processes already present in living cells (i.e. translocation processes). Therefore, nanopore technology has become a fundamental field of interest to molecular biologists and biochemists alike.

It has been demonstrated that a voltage gradient can drive single-stranded biopolymers through a transmembrane channel, or nanopore (See Kasianowicz et al., "Characterization of individual polynucleotide molecules using a membrane channel", Proc. Natl. Acad. Sci. USA, 93: 13770-13773, 1996). During the translocation process, the extended biopolymer molecule will block a substantial portion of the otherwise open nanopore channel. This blockage leads to a decrease in the ionic current flow of the buffer solution through the nanopore during the biopolymer translocation. The passage of a single biopolymer can be monitored by recording the translocation duration and the blockage current, yielding plots with predictable stochastic sensing patterns. From the uniformly controlled translocation conditions, the lengths of the individual biopolymers can be determined from the translocation time. Furthermore, the differing physical and chemical properties of the individual monomers of the biopolymer strand may generate a measurable and reproducible modulation of the blockage current that allows an identification of the specific monomer sequence of the translocating biopolymer. These initially proposed systems suffer from a number of problems. For instance, some of the proposed systems require the self-assembly of pore forming proteins on membranes (i.e. α-hemolysin). Reproducibility of membranes and systems has been quite problematic. Secondly, commercial products require robustness not present in sensitive systems that require fluctuations of ionic currents for measurements. For these reasons, recent research has focused more on solid-state pore techniques that have an ability for high reproducibility and ease of fabrication. Such techniques as "ion beam sculpting" have shown some promise in fabricating molecular scale holes and nanopores in thin insulating solid-state membranes. These pores have also been effective in localizing molecular-scale electrical junctions and switches (See Li et al., "Ion beam sculpting at nanometer length scales", Nature, 412: 166-169, 2001).

These techniques have shown similar consistent results and current blockage with double stranded DNA reminiscent of ionic current blockages observed when single stranded DNA are translocated through the channel formed by α-hemolysin in a lipid bilayer. The duration of these blockages have been on the millisecond scale and current reductions have been to 88% of the open-pore value. This is commensurate with translocation of a rod-like molecule whose cross-sectional area is 3-4 $nm^2$ (See Li et al., "Ion beam sculpting at nanometer length scales", Nature, 412: 166-169, 2001). This methodology, however, suffers from the limitation that only crude measurements of the presence or absence of the translocating polymer can be made. In addition, these systems are incapable of actually determining the primary sequences (order of monomeric units) of the translocating biopolymer.

A second approach has been suggested for detecting a biopolymer translocating a nanopore in a solid-state material such as $Si_3N_4$. However, it is well known that the tunneling current has an exponential dependence upon the height and width of the quantum mechanical potential barrier to the tunneling process. This dependence implies an extreme sensitivity to the precise location in the pore of the translocating molecule. Both steric attributes and physical proximity to the tunneling electrode could cause changes in the magnitude of the tunneling current which would be far in excess of the innate differences expected between different base-types under ideal conditions. For this reason, it is difficult to expect the simplest tunneling configurations to have the specificity required to perform sequencing.

Although there are a number of important techniques for nanopore sequencing being developed, there still remains problems regarding getting the actual biopolymer to the nanopore. In addition, there remains the issue of actually threading the biopolymer into the nanopore so that its sequence may be accurately determined. A few techniques have been developed to potentially address this issue. For instance, the application of hydrodynamics and pressure applied to a closed system has been considered for directing biopolymers into nanopore structures. These inventions have a number of limitations not limited to increase in cost and safety. Secondly, some work has focused on use of electric fields to potentially draw the biopolymer through the nanopore structure. A problem with such techniques is that the biopolymer does not easily move through such defined spaces unless it is at first "threaded" into or through the nanopore. Some work has been done on passing biopolymers through fabricated nanopores in membranes of silicon nitride or silicon dioxide. Further, there is the continual need to monitor the position of the biopolymer in the nanopore as well as having the end of the biopolymer enter the nanopore as opposed to the middle of the material. In addition, there is the need to control the motion of the biopolymer in the nanopore as well as to stretch or extend the biopolymer in the nanopore so that it may be correctly and accurately sequenced. These and other problems with the prior art processes and designs are obviated by the present invention. The references cited in this application infra and supra, are hereby incorporated in this application by reference. However, cited references or art are not admitted to be prior art to this application.

SUMMARY OF THE INVENTION

The invention provides a method and apparatus for threading a biopolymer into and through a nanopore. The apparatus for threading the biopolymer through a nanopore, comprises a substrate having a first channel with a channel wall and a nanopore in the channel wall, the channel wall and nanopore being designed for receiving a biopolymer, a first set of electrodes for moving the biopolymer in a first direction past the nanopore, and a second set of electrodes for moving the biopolymer in a second direction through the nanopore after the biopolymer has been moved past the nanopore.

The invention also provides a method for threading a biopolymer through a nanopore. The method comprises moving the biopolymer past the nanopore in a first direction, and threading the biopolymer through the nanopore in a second direction.

BRIEF DESCRIPTION OF THE FIGURES

The invention is described in detail below with reference to the following figures.

DETAILED DESCRIPTION OF THE INVENTION

Figure 1A:
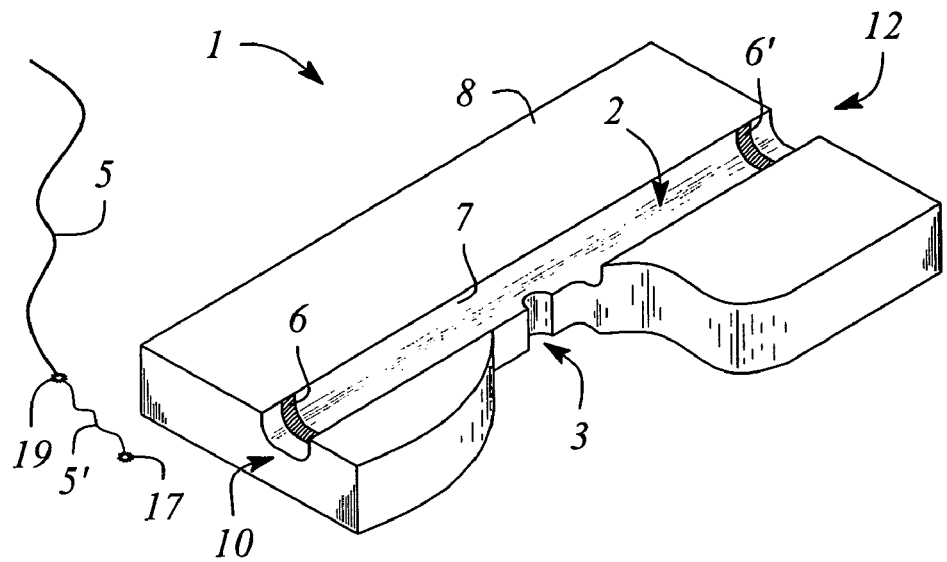
FIG. 1A shows a schematic representation of a first embodiment of the present invention.

Before describing the present invention in detail, it is to be understood that this invention is not limited to specific compositions, method steps, or equipment, as such may vary. It is also to be understood that the terminology used herein is for the purpose of describing particular embodiments only, and is not intended to be limiting. Methods recited herein may be carried out in any order of the recited events that is logically possible, as well as the recited order of events. Furthermore, where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

Unless defined otherwise below, all technical and scientific terms used herein have the same meaning as commonly understood by one of ordinary skill in the art to which this invention belongs. Still, certain elements are defined herein for the sake of clarity.

It must be noted that, as used in this specification and the appended claims, the singular forms "a", "an" and "the" include plural referents unless the context clearly dictates otherwise. Thus, for example, reference to "a biopolymer" includes more than one biopolymer, and reference to "a voltage source" includes a plurality of voltage sources and the like. In describing and claiming the present invention, the following terminology will be used in accordance with the definitions set out below.

A "biopolymer" is a polymer of one or more types of repeating units. Biopolymers are typically found in biological systems and particularly include polysaccharides (such as carbohydrates), peptides (which term is used to include polypeptides and proteins), glycans, proteoglycans, lipids, sphingolipids, known biologicals materials such as antibodies, etc. and polynucleotides as well as their analogs such as those compounds composed of or containing amino acid analogs or non-amino acid groups, or nucleotide analogs or non-nucleotide groups. This includes polynucleotides in which the conventional backbone has been replaced with a non-naturally occurring or synthetic backbone, and nucleic acids (or synthetic or naturally occurring analogs) in which one or more of the conventional bases has been replaced with a group (natural or synthetic) capable of participating in hydrogen bonding interactions, such as Watson-Crick type, Wobble type and the like. Polynucleotides include single or multiple stranded configurations, where one or more of the strands may or may not be completely aligned with another. A "nucleotide" refers to a sub-unit of a nucleic acid and has a phosphate group, a 5 carbon sugar and a nitrogen containing base, as well as functional analogs (whether synthetic or naturally occurring) of such sub-units which in the polymer form (as a polynucleotide) can hybridize with naturally occurring polynucleotides in a sequence specific manner analogous to that of two naturally occurring polynucleotides. Biopolymers include DNA (including cDNA), RNA, oligonucleotides, and PNA and other polynucleotides as described in U.S. Pat. No. 5,948,902 and references cited therein (all of which are also incorporated herein by reference), regardless of the source. An "oligonucleotide" generally refers to a nucleotide multimer of about 10 to 100 nucleotides in length, while a "polynucleotide" includes a nucleotide multimer having any number of nucleotides. A "biomonomer" references a single unit, which can be linked with the same or other biomonomers to form a biopolymer (e.g., a single amino acid or nucleotide with two linking groups one or both of which may have removable protecting groups).

A "substrate" refers to any surface that may or may not be solid and which is capable of holding, embedding, attaching or which may comprise the whole or portions of an electrode.

"Hybridizing", "annealing" and "binding", with respect to polynucleotides, are used interchangeably. "Binding efficiency" refers to the productivity of a binding reaction, measured as either the absolute or relative yield of binding product formed under a given set of conditions in a given amount of time. "Hybridization efficiency" is a particular sub-class of binding efficiency, and refers to binding efficiency in the case where the binding components are polynucleotides. It will also be appreciated that throughout the present application, that words such as "upper", "lower" are used in a relative sense only. A "set" may have one type of member or multiple different types. "Fluid" is used herein to reference a liquid.

The term "in" refers to being "within" and/or a portion that may also be exterior to. For instance, a biopolymer "in" a nanopore may mean that the whole biopolymer is within the opening of the nanopore or only a small portion of the biopolymer is located near the nanopore with a substantial portion protruding exterior to the nanopore.

The term "nanopore" refers to any pore or hole between at least a pair of electrodes or a hole in a solid substrate. Nanopores can range in size and can range from 1 nm to around 300 nm. Most effective nanopores have been roughly around 2 mm.

The term "translocation" or to "translocate" refers to movement from one side to another, movement in a defined direction. Any action or biopolymer following along a vector that has velocity and direction.

The term "portion" or "portion of a biopolymer" refers to a part, subunit, monomeric unit, portion of a monomeric unit, atom, portion of an atom, cluster of atoms, charge or charged unit.

The term "voltage gradient" refers to having the ability to establish a potential between any two electrodes.

The term "adjacent" refers to anything that is near, next to or adjoining. For instance, a nanopore may be near an electrode, it may be next to the electrode, it may pass through an electrode or it may be adjoining the electrode. This would include spacing in linear, two-dimensional and three-dimensional space.

Figure 1B:
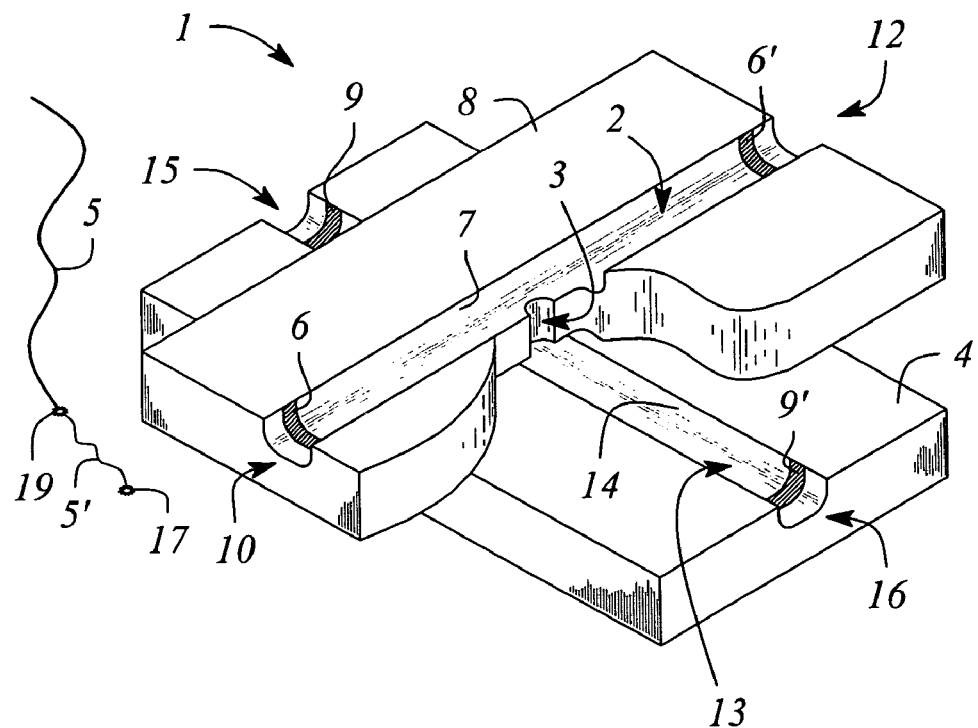
FIG. 1B shows a schematic representation of a second embodiment of the invention.
Figure 1C:
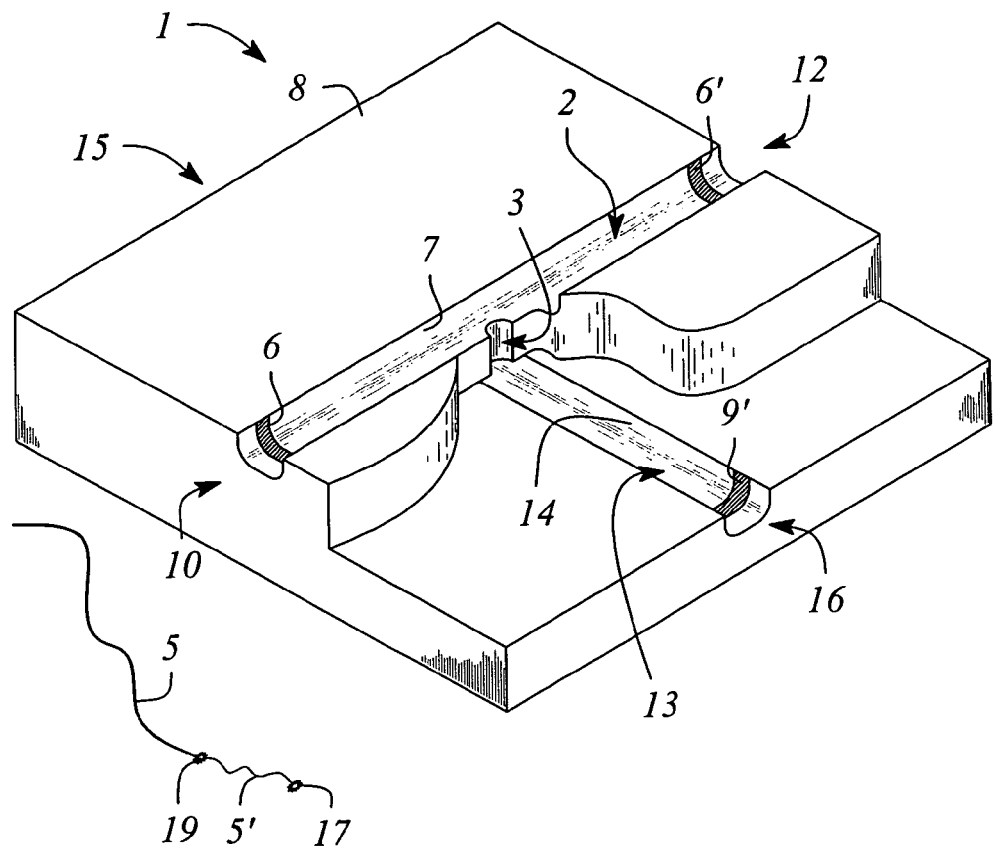
FIG. 1C shows a schematic representation of a third embodiment of the invention
Figure 1D:
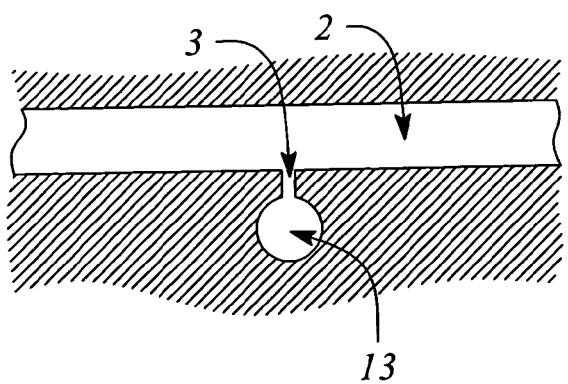
FIG. 1D shows a cross sectional view of the third embodiment of the invention.
Figure 2:
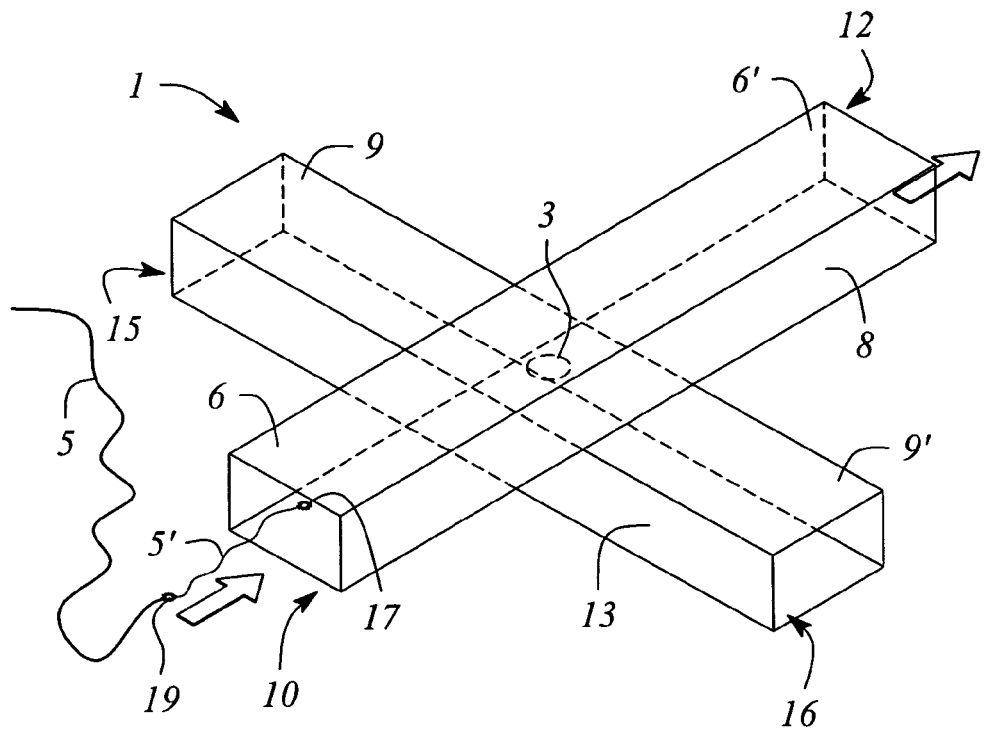
FIG. 2 shows a fourth embodiment of the present invention.

Referring now to FIGS. 1-2, the present invention provides a biopolymer threading apparatus 1 for threading a biopolymer 5 through a nanopore 3. The biopolymer apparatus 1 may be employed under ambient conditions or in solution. Note that FIGS. 1A-1C show schematic representations of the present invention with related open or exposed channels. For clarity the channels are depicted in this open format, and both nanopore 3 and the portion of channel 2 near nanopore 3 are shown in a cutaway view. The invention should not be interpreted to these literal depictions. For instance, the channels and substrates may also be completely enclosed or within a substrate or other similar type material.

In a first embodiment of the invention, the biopolymer threading apparatus 1 comprises a substrate 8 having a first channel 2 defined in the substrate 8. The first channel 2 defines a channel wall 7. A nanopore 3 is positioned in the first channel wall 7. The first channel 2 may run the length of the substrate 8 or may comprise a portion of it. The first channel 2 may comprise any number of different shapes and sizes. The shape and size of the first channel 2, is not important to the invention. The first channel 2 comprises a first end 10 and a second end 12 opposite the first end 10. The channel wall 7 and nanopore 3 are designed for receiving the biopolymer 5. Although the figure shows a single contiguous substrate, various substrates may be employed. For instance, a second substrate 4 or additional substrates may be employed adjacent to the substrate 8 (See FIGS. 1A-1C. Channel 2 may be part of a continuous open path defined by channel 2 and by additional channels or capillaries, not shown, connected in series with channel 2 via channel ends 10 and 12. Such additional channels or capillaries may include known and unknown methods of straightening molecules before they approach channel 2 during operation of the invention. However, the substrate 8 must have a channel 2 with a nanopore 3 that is capable of receiving a biopolymer 5. FIGS. 1A-1C show an example of how two separate channels can communicate through the nanopore 3. The second channel 13 communicates directly with the first channel 7 by way of the nanopore 3. Channel 13 may be part of a continuous open path defined by channel 13 and by additional channels or capillaries, not shown, connected in series with channel 13 via channel ends 15 and 16.

The biopolymer threading apparatus 1 may also comprise one or more means for moving the biopolymer in a defined direction. Any number of devices or techniques are known in the art for moving biopolymers. For instance, the means may comprise devices that use electrophoretic flow, electroosmotic flow, electrokinetic flow, sheath flow, plug flow, parabolic flow, Hagen-Poiseuille flow, hydrostatic pressure, electrohydrodynamic flow, reptation, osmotic gradients, diffusion, electric fields, hydrodynamic pressure, pressure, or other physical and chemical properties well known for moving or separating biopolymers. For instance, a set of electrodes 6, 6' may be located in the channel wall 7 for moving the biopolymer 5 in a first direction past the nanopore 3. In addition, a second set of electrodes 9, 9' may be located in a second channel 13 adjacent to the nanopore 3 for threading the biopolymer 5 through the nanopore 3 or moving the biopolymer 5 in a second direction. An optional additional set of electrodes may be employed for sequencing the biopolymer as it passes through the nanopore 3 in the channel wall 7 (not shown in FIGS.). For information on the devices used for sequencing and control of the biopolymer in the nanopore see application Ser. No. 10/352,675 entitled "Apparatus and Method for Biopolymer Identification During Translocation Though a Nanopore", Ser. No. 10/355,347 entitled "Apparatus and Method for Control of Biopolymer Translocation Through a Nanopore", and related continuation in part application of Ser. No. 10/352,675 filed on Jun. 12, 2003 entitled "Nanopore with Resonant Tunneling Electrodes" (all which are herein incorporated by reference in their entirety).

It should be noted that electrodes 6, 6' need only be located in the continuous open path of which channel 2 is a portion, and need not be located within the confines of channel 2 itself. Likewise, it should be noted that electrodes 9, 9' need only be located in the continuous open path of which channel 13 is a portion, and need not be located within the confines of channel 13 itself. Nor do electrodes 6, 6', 9, 9' need to be contiguous with their respective channel walls 7 and 14, but instead may stand away from the walls in their respective continuous flow paths. The representation of the electrodes 6, 6' in channel 2, and of electrodes 9, 9' in channel 13, as shown in FIGS. 1A-1C is merely for the purposes of compactness and clarity.

The electrodes 6, 6' are electrically connected through a voltage source 11 (not shown in FIGS.), and the electrodes 9, 9' are electrically connected through a voltage source 11' (not shown in FIGS.). A third voltage source 11" (not shown in FIGS.) may be employed so that one of the electrode set 6,6' is electrically connected to one of the second set of electrodes 9,9'. This is an option and not a requirement of the invention. The biopolymer threading apparatus 1 and associated parts may be designed in a variety of sizes and shapes. For instance, the apparatus, channels and substrates may be designed on the micro or nano scale. Having described the invention generally, a description of the details of each component of the invention is now in order.

The biopolymer 5 may comprise a variety of shapes, sizes and materials. The shape or size of the molecule is not important, but it must be capable of translocation through the nanopore 3. For instance, both single stranded and double stranded RNA and DNA may be used as a biopolymer 5. In addition, the biopolymer 5 may contain groups or functional groups that are charged. Furthermore, metals or materials may be added, doped or intercalated within the biopolymer 5 to provide a net dipole, a charge or allow for conductivity through the biopolymer. The material of the biopolymer may allow for electron tunneling between optional electrodes placed adjacent to the nanopore opening. It is important to the invention that the biopolymer 5 comprise a leader molecule 5' for threading the biopolymer into the nanopore 3. The leader molecule 5' allows for threading the biopolymer before its sequence is determined. The leader molecule 5' also provides a way to track the positioning of the biopolymer 5 in the nanopore 3.

The first electrode set 6,6' and the second electrode set 9,9' may comprise a variety of electrically conductive materials. Such materials include electrically conductive metals and alloys of platinum, iridium, palladium, gold, mercury, mercury calomel, tin, copper, zinc, iron, magnesium, cobalt, nickel, and vanadium and various combinations thereof. Other materials well known in the art that provide for electrical conduction may also be employed. The first electrode set 6, 6' creates an electric field that provides some combination of electrokinetic movement of the biopolymer 5 within the fluid in channel 2 electroosmotic movement of fluid within channel 2. The movement of the biopolymer 5 with respect the channel 2 may be purely due to electroosmotic flow of the liquid surrounding the biopolymer 5, or may be purely due to electrokinetic movement of the biopolymer 5 within the liquid, or may have components due to both This combination of electroosmotic movement and electrokinetic movement is referred to herein as field-driven movement, and may include effects arising from the presence of spatial gradients in the electric field. The biopolymer is drawn into the first channel 2 in a first direction from the first end 10 to the second end 12 of the first channel 2. The first channel 2 is of sufficient length that the biopolymer 5 may be extended linearly as it is drawn closer to the second end 12 of the first channel 2 and past the nanopore 3.

The second electrode set 9, 9' may comprise the same or similar materials as described above for the first electrode set 6, 6'. As discussed above, its shape, size and positioning may be altered relative to the first electrode and the nanopore 3. The second electrode set 9, 9' is designed similarly to the first electrode set 6, 6'. However, the second electrode set 9, 9' is positioned in the second channel 13. The second channel 13 may also comprise a second channel wall 14. The second channel 13 may comprise a first end 15 and a second end 16. In addition, the second channel 13 may be oriented in a different direction from the first channel 2. For instance, the second channel 13 may be positioned orthogonal to the first channel 7. This is not a requirement of the invention and should not be interpreted to limit the broad scope of the invention. The second channel 13 communicates with the first channel 2 by way of the nanopore 3 in the first channel wall 7. The second channel 13 is adjacent to the first channel 2 and in certain embodiments may be positioned below the first channel 2. The second electrode set 9, 9' creates an electric field that draws the biopolymer 5 and leader molecule 5' through the nanopore 3 in the first channel wall 7. The electric field creates field-driven movement of the biopolymer 5 through the nanopore 3 of the channel wall 7 toward the second end 16 of the second channel 13. The electric field draws the biopolymer 5 through the nanopore 3 of the channel wall 7 and the biopolymer 5 may then be sequenced. Sequencing can then occur as the biopolymer 5 is being drawn through the nanopore 3.

The substrate 8 may comprise a variety of materials known in the art for designing substrates and nanopores. The substrate 8 may or may not be a solid material. For instance, the substrate 8 may comprise a mesh, wire, or other material that a nanopore may be constructed. Such materials may comprise silicon, silica, solid-state material such as $Si_3N_4$, silicon-rich silicon nitride, silicon oxynitride, carbon based materials, plastics, metals, or other materials known in the art for etching or fabricating semiconductor or electrically conducting materials. The solid substrate 8 may comprise various shapes and sizes. However, it must be large enough and of sufficient width to be capable of forming the nanopore 3 through it.

The nanopore 3 may be positioned anywhere on/through the substrate 8. The nanopore may range in size from 1 nm to as large as 300 nm. In most cases, effective nanopores for identifying and sequencing biopolymers would be in the range of around 2-20 nm. These size nanopores are just large enough to allow for tranlocation of a biopolymer 5. The nanopore 3 may be established using any methods well known in the art. For instance, the nanopore 3, may be sculpted in the substrate 8, using argon ion beam sputtering, etching, photolithography, or other methods and techniques well known in the art.

The voltage sources 11, 11', and 11" may be positioned anywhere relative to the substrate 8, the nanopore 3, the first electrode set 6,6' and the second electrode set 9,9'. The voltage sources 11, 11', and 11" should be capable of establishing a voltage gradient between the respective electrodes to which they are connected. A variety of voltage sources 11, 11', and 11" may be employed with the present invention. A number of these voltage sources are known in the art, and are particularly known to those skilled in patch-clamp techniques.

Having now described the apparatus of the invention in detail, a discussion of the method is now in order. The method of the present invention provides a way for threading a biopolymer 5 through a nanopore 3 in a substrate 8. The method comprises applying a first electric field in a defined direction to move the leader molecule 5' past the nanopore 3 in the substrate 8 until a portion of the leader molecule 5' is adjacent to the nanopore 3 and applying a second electric field in a second direction to move the leader molecule 5' in a second direction through the nanopore 3 so that the biopolymer 5, being attached to the leader molecule 5', follows the leader molecule 5' through the nanopore. Advantageously, the leader molecule 5' may be sufficiently thin and flexible so that a central portion of the leader molecule 5', being in an extended position across the nanopore 3 in channel 2, can double upon itself to pass through the nanopore 3 into channel 13. The biopolymer 5, even if it is stiffer and of larger diameter than the leader molecule 5', can then follow the leader molecule 5' so that all or a portion of biopolymer 5 extends through the nanopore 3 and into channel 13.

Advantageously, the leader molecule 5' may incorporate along its length one or more light-emitting moieties such as fluorophores or fluorescent nanoparticles. The biopolymer threading apparatus 1 may be transparent so that light may be used to detect one or more optional fluorophores on the leader molecule 5'. If channel 13 is in a direction other than that of channel 2, such as orthogonal to channel 2, it is then possible to see with an optical microscope, in real time, that the fluorophore has transited from channel 2 to channel 13, providing an indication that the portion of the leader molecule 5' containing the fluorophore has also transited the nanopore. This method of microscopic optical tracking can be employed as discussed in more detail below.

FIG. 2 shows a wire frame view of a fourth embodiment of the present invention (note: FIGS. 2 and 3 need added notation of the channel 2 feature). The embodiment of FIG. 2 is shown again in FIGS. 3A-3D.

Figure 3A:
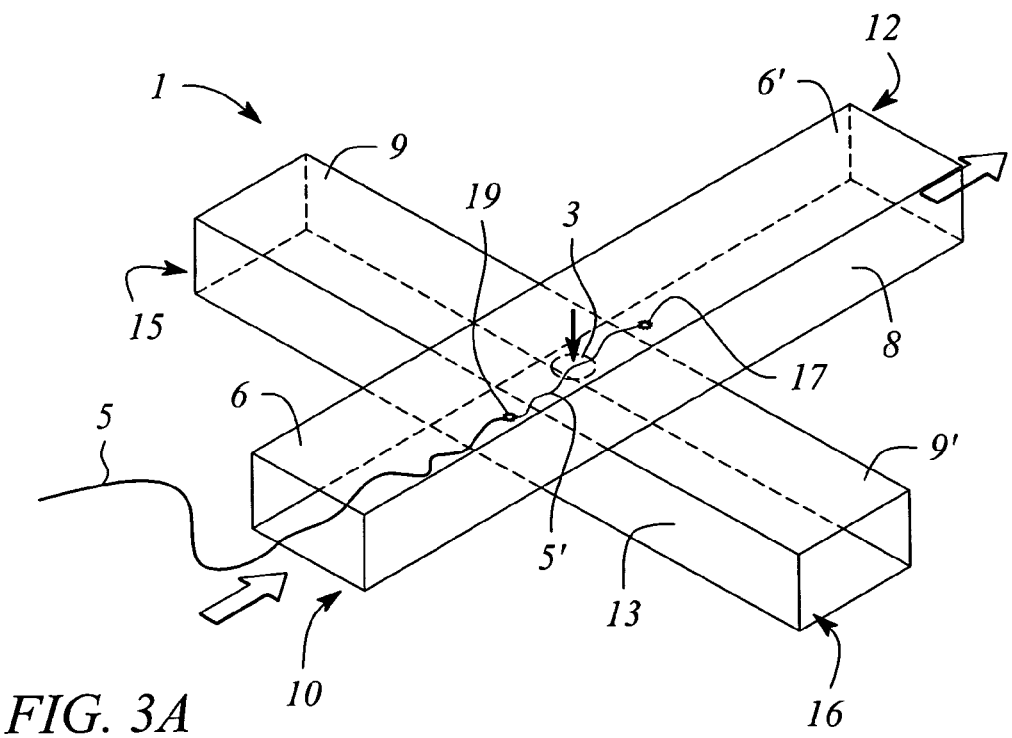
FIG. 3A shows a first step of the method of the present invention.

FIG. 3A shows a first step of the method of the present invention. The biopolymer 5 comprises a leader molecule 5'. The leader molecule 5' is located at the first end of the biopolymer 5. The leader molecule 5' comprises a portion of the biopolymer 5 that is not important for sequencing. Advantageously, the leader molecule 5' may have an electrical charge per unit length different than, being either greater than or less than, the electrical charge per unit length of the rest of the biopolymer 5. If such a difference in electrical charge per unit length is present, the leader molecule 5' will tend to precede the rest of the biopolymer 5 as biopolymer 5 moves due to field-driven movement along channel 2 in the direction depicted by the white arrows in FIG. 3A. For example, if the portion of the biopolymer 5 aside from the leader 5' is a double-stranded chain of DNA, (dsDNA chain) each of the bases in the dsDNA chain has one negative electron charge. The leader molecule 5' may then comprise an alkane chain with one or more negatively charged groups attached to each of the carbon atoms in the alkane chain, providing a greater negative charge per unbit length than the dsDNA portion of the biopolymer 5. It will be appreciated that all of the charges along the length of biopolymer 5, including leader molecule 5', must be of the same sign, either positive or negative, because if not then the attraction of positive charges to negative charges will tend to ball up the entire biopolymer 5.

The leader molecule 5' may comprise one or more tracking molecules such as first fluorophore 17 and second fluorophore 19. The first fluorophore 17 may be at a first end of the leader molecule 5', while the second fluorophore 19 may be at a second end of the leader molecule 5' of biopolymer 5. The biopolymer 5 and leader molecule 5' are drawn into the channel 2 by way of an electric field created by the first set of electrodes 6, 6' that may be positioned on either end of the channel 2. The electric field creates field-driven movement between the set of electrodes 6, 6'. The first fluorophore 17 and the second fluorophore 19 provide optical knowledge of the position of the leader molecule 5' of biopolymer 5. The walls of the channel may be transparent for detecting a fluorophore's position more easily. Brownian motion causes the leader molecule to move back and forth across the nanopore 3 in a direction generally perpendicular to the length of channel 2. Field-driven movement draws the biopolymer 5 and leader molecule 5' past the nanopore 3.

Figure 3B:
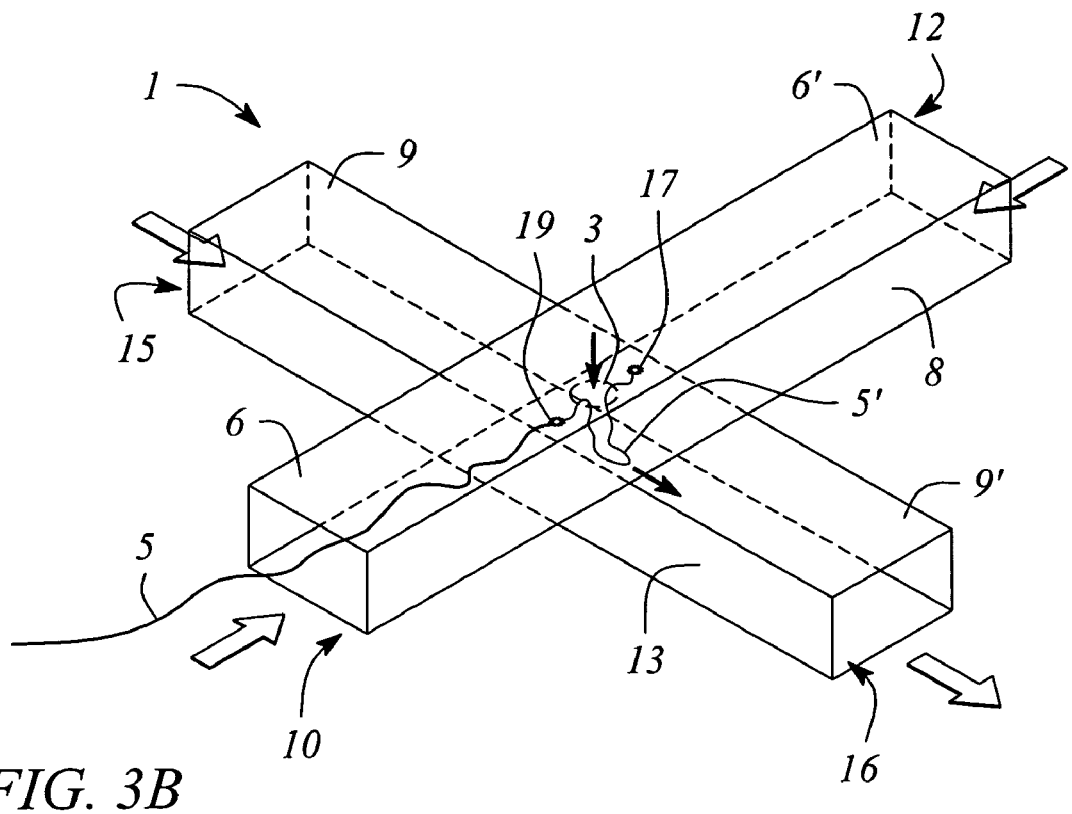
FIG. 3B shows a second step of the method of the present invention.

FIG. 3B shows a second step of the method of the present invention. In this step of the invention, the applied voltages are changed. The voltage difference between electrodes 6 and 6' is reduced, and the voltage difference between electrodes 9 and 9' is increased to create field-driven movement through the nanopore 3, and along channel 13 in the direction indicated by the white arrows at channel ends 15 and 16. In this case the portion of the leader molecule 5' trailing the first end of the leader molecule 5' is sufficiently close to the nanopore 3, during some portions of its movement back and forth across nanopore 3 where the nanopore 3 intersects channel 2, that the effective force of the electric field can be felt by the leader molecule 5' traversing the nanopore 3. At some point, the leader molecule 5' of the biopolymer 5 falls within a capture range of the electric field extending through nanopore 3 from channel 2 to channel 13, and the central portion of the leader molecule 5' is drawn into the second channel 13, doubling on itself as it passes through the nanopore 3, and drawing the portion of biopolymer 5 to be sequenced closer to the nanopore 3. Field-driven movement is established in the second channel 13, drawing doubled portion of the leader molecule 5' along the length of the second channel 13. Both fluorophores still sitting in channel 2 and are move closer to the nanopore 3 eventually drawn through the nanopore 3. Either the first fluorophore 17 is threaded through the nanopore 3 followed by the second flourophore 19, or vice-versa. In either case, an observer using a microscope can see that both fluorophores have passed through the nanopore, and so can confirm that a portion of biopolymer 5 extends through the nanopore.

Figure 3C:
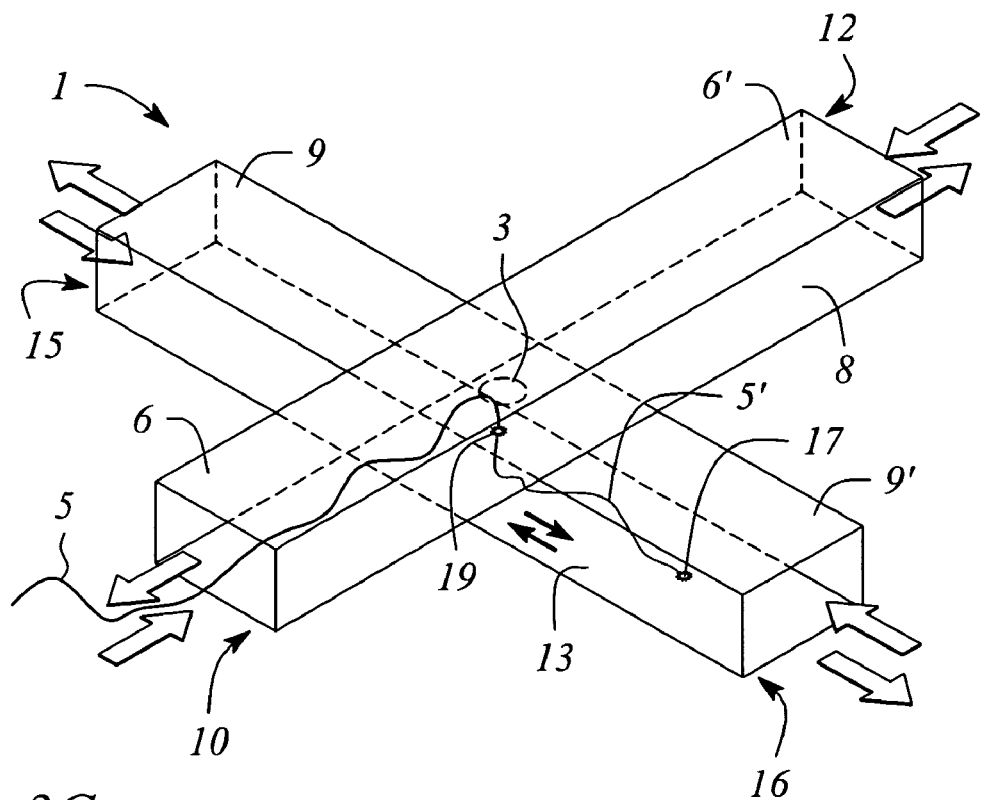
FIG. 3C shows a third step of the method of the present invention.

FIG. 3C shows the third step of the method of the present invention. In this step, both the first fluorophore 17 and the second fluorophore 19 have passed through the nanopore 3, providing information that the entire leader molecule 5' has passed through the nanopore 3 and that the biopolymer 5 is properly in position for sequence determination by the nanopore 3. If the fluorophores fluoresce at the same wavelength or at different wavelengths, the location of the biopolymer 5 can be determined with some precision. This is contingent on the requirement that the second channel 13 is transparent.

It will be evident to those skilled in the art of using nanopores that any electric field extending through the nanopore from channel 2 to channel 13 will decrease greatly in magnitude at distances of a few nanopore diameters away from the entrance and exit of the nanopore, and so in each of channels 2 and 13, electric fields created by electrode sets 6, 6' and 9, 9' respectively can be largely independent of one another. Thus it is possible to set up in each of channels 2 and 13 an electric field that, by field-driven movement, can pull or push on the portion of biopolymer 5 in the respective channel, independently of the corresponding push or pull on the portion of biopolymer 5 in the respective other channel. Thus field-driven movement can be established in either direction in both the channel 2 and the second channel 13, as indicated by the arrows pointing in both directions at channels ends 10, 12, 15, and 16. The motion of the biopolymer 5 can be established in either direction and biopolymer 5 can be stretched by varying amounts while it extends through the nanopore 3.

Advantageously, one or more additional light emitting moieties, not shown, may be present along the length of biopolymer 5 in regions separate from leader molecule 5'. The presence of such additional light emitting moieties can give additional information about the position and state of stretch of biopolymer 5.

After the leader molecule 5' has passed through the nanopore 3, the remaining portion of the biopolymer 5 will be in a position to be sequenced by the nanopore 3 and electrodes that may be positioned adjacent to the nanopore 3.

Figure 3D:
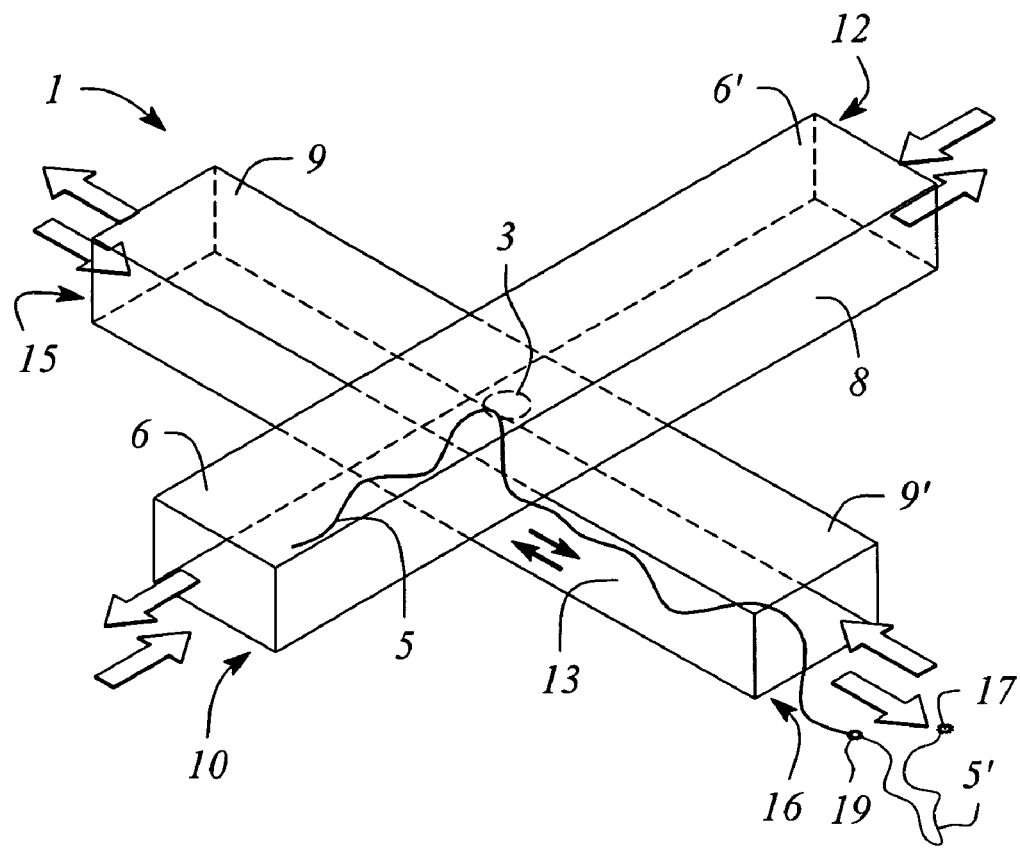
FIG. 3D shows a final step of the method of the present invention.

FIG. 3D shows the final step of the method of the present invention. This step simply shows the further migration of the biopolymer 5 and leader sequence 5' down the second channel 13 after sequencing has begun.

Figure 4A:
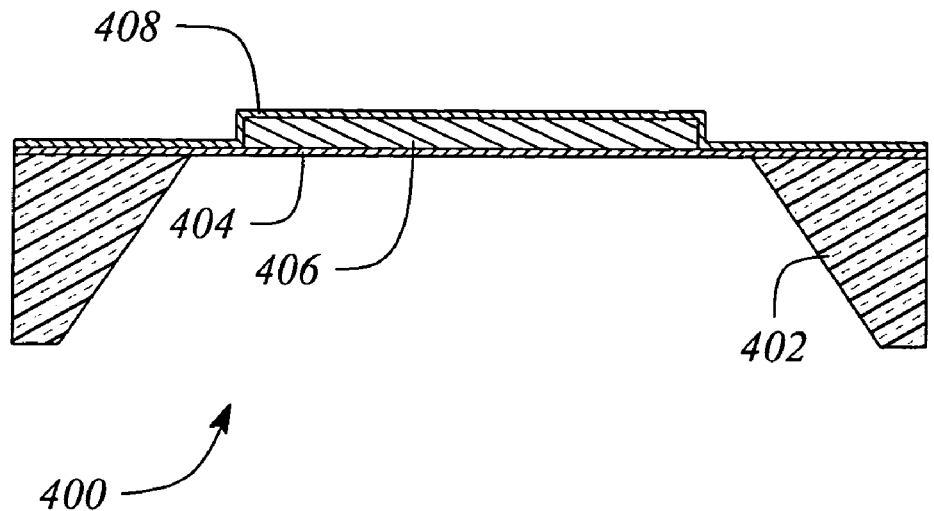
FIGS. 4A-4E show in detail a method of fabricating an embodiment of the present invention.

FIGS. 4A-4E show a method of building an embodiment 400 of the present invention. FIG. 4A is a cross section showing a silicon chip 402 that is part of a larger silicon wafer, not shown. The silicon chip 402 has been etched to leave a freestanding window 404 comprising, for example, silicon nitride. A region 406 of photoresist is defined on window 404 via standard lithographic techniques, and a layer 408 comprising, for example, silicon oxynitride is deposited over the top surface, for example at a low temperature of 95 C. It will be appreciated that region 406 extends out of the plane of the drawing and can have openings not shown in the drawing accessible to solvents for removing the photoresist from region 406.

Figure 4B:
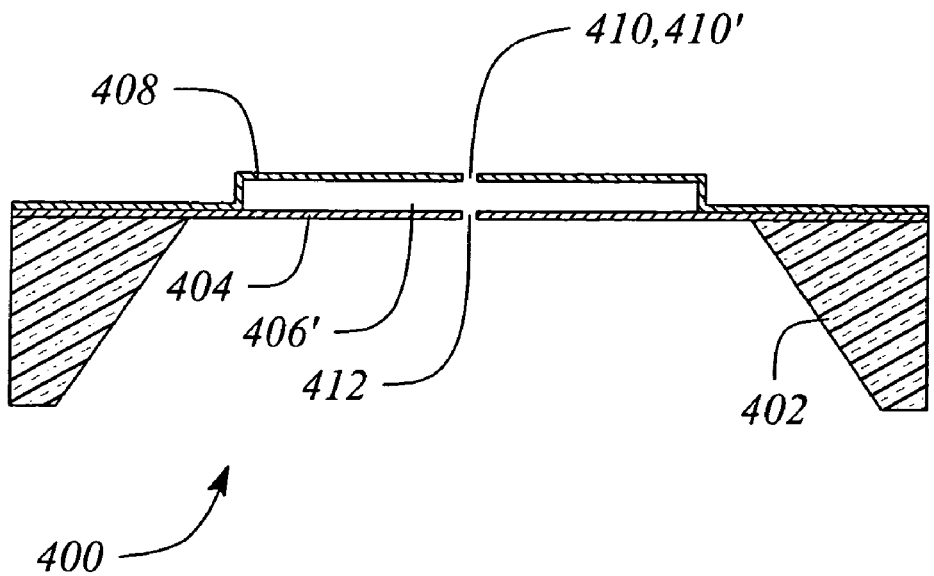

FIG. 4B shows embodiment 400 after such solvents have been used to remove the photoresist from region 406, leaving region 406' as an open channel which corresponds to channel 13 as discussed for the embodiments 1 shown in FIGS. 1-3. A focused ion beam (FIB) is then used to drill a hole through layers 408 and 404, creating holes 410 and 412. Ion beam sculpting in a low-energy argon beam is used to reduce the diameter of a portion of hole 410, creating nanopore 410'. Nanopore 410' corresponds to nanopore 3 as discussed for the embodiments 1 shown in FIGS. 1-3. At this point in the fabrication process the nanopore 410' can be instrumented with sensing features, for example as discussed in application Ser. No. 10/352,675 entitled "Apparatus and Method for Biopolymer Identification During Translocation Though a Nanopore", Ser. No. 10/355,347 entitled "Apparatus and Method for Control of Biopolymer Translocation Through a Nanopore", and related continuation in part application of Ser. No. 10/352,675 filed on Jun. 12, 2003 entitled "Nanopore with Resonant Tunneling Electrodes" (all which are herein incorporated by reference in their entirety).

Figure 4C:
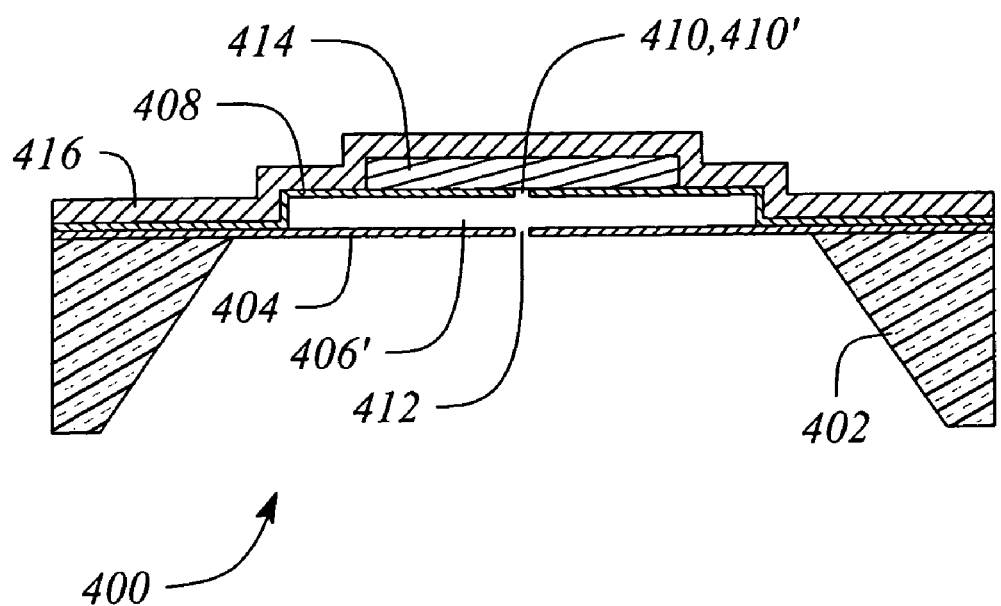

The fabrication process continues as shown in FIG. 4C. A region 414 comprising, for example, photoresist is defined by standard lithographic techniques, and a layer 416 comprising, for example, silicon oxynitride is deposited over the exposed surface of the device, for example at a low temperature of 95 C. It will be appreciated that region 414 extends out of the plane of the drawing and can have openings not shown in the drawing accessible to solvents for removing the photoresist from region 414

Figure 4D:
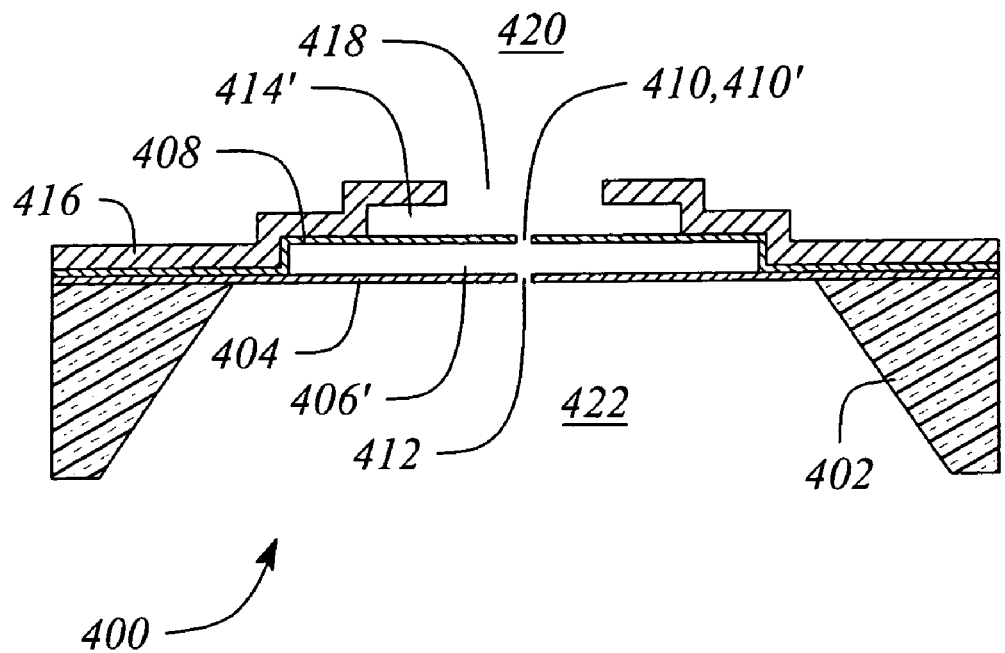

FIG. 4D shows the continuation of the fabrication process. Optionally for purposes of visibility and photoresist removal, hole 418 is opened in layer 416, exposing the photoresist in region 414 which can then be removed by solvents to leave open channel region 414'. Region 414' corresponds to channel 2 as discussed for the embodiments shown in FIGS. 1-3. At this point in the fabrication process embodiment 400 corresponds to the embodiments 1 shown in FIGS. 1-3, with additional features comprising hole 412 and hole 418.

Figure 4E:
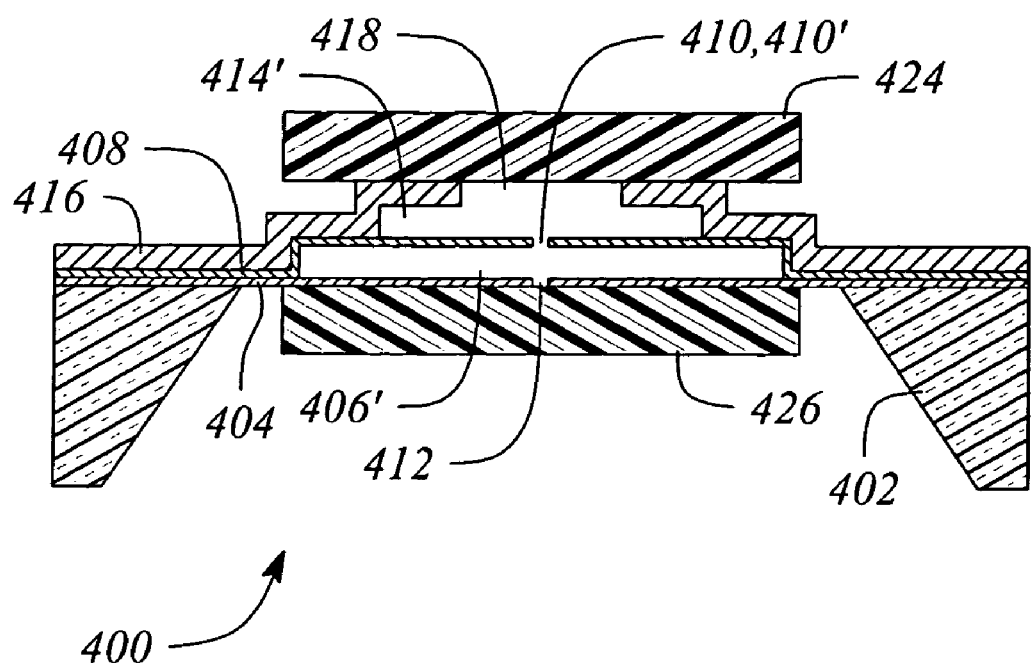

Hole 412 or hole 418, or both, may be left in place connecting embodiment 400 to respective regions 422 and 420, and embodiment 400 will function as desired. Alternatively, as shown in FIG. 4E, cover slip 424 may be placed over hole 418, or cover slip 426 may be placed over hole 412, or both cover slips may be used. Also, optional hole 418 may be omitted from the fabrication process.

We claim:

1. An apparatus for threading a biopolymer through a nanopore, comprising:
    (a) a first microfluidic channel having at least two electrodes for creating an electric field for creating electrophoretic movement of the biopolymer in a first direction;
    (b) a nanopore in the wall of the first microfluidic channel; and
    (c) a second microfluidic channel communicating with the first microfluidic channel by way of the nanopore in the wall of the first microfluidic channel, the second microfluidic channel having a second set of electrodes for creating electrophoretic movement of the bipolymer in a second direction;
    wherein at least one of the electrodes of the second set of electrodes is located in the second microfluidic channel on the opposite side of the nanopore with respect to at least one other of the electrodes of the second set of electrodes.

2. An apparatus as recited in claim 1, wherein the first channel diameter is from 1 to 10 micrometers.

3. An apparatus as recited in claim 1, wherein the first channel wall through which the nanopore passes is from 1 to 10 micrometers in width.

4. A method of threading a biopolymer through an apparatus as recited in claim 1, comprising:
    (a) moving the biopolymer past the nanopore in a first direction; and
    (b) threading the biopolymer through the nanopore in a second direction.

5. An apparatus for threading a biopolymer through a nanopore, comprising:
    (a) a substrate having a channel etched in a first surface thereof, a channel wall comprising a first surface of said substrate and a nanopore in the channel wall, said nanopore connecting said channel to a second surface of said substrate, the channel wall and nanopore being designed for receiving a biopolymer;
    (b) means for moving the biopolymer toward the nanopore in a first direction; and
    (c) means for threading the biopolymer through the nanopore in a second direction.

6. An apparatus for threading a biopolymer through a nanopore, comprising:
    (a) a substrate having a channel etched in a first surface thereof, a channel wall comprising a first surface of said substrate and a nanopore in the channel wall, said nanopore connecting said channel to a second surface of said substrate, the channel wall and nanopore being designed for receiving a biopolymer;
    (b) at least one set of electrodes disposed in said first channel for moving the biopolymer in a first direction past the nanopore; and
    (c) at least one set of electrodes for moving the biopolymer in a second direction through the nanopore after the biopolymer has been moved past the nanopore.

7. An apparatus as recited in claim 6, wherein the biopolymer comprises a polynucleotide.

8. An apparatus as recited in claim 7, wherein the polynucleotide is double stranded.

9. An apparatus as recited in claim 7, wherein the polynucleotide is selected from the group consisting of mRNA, DNA, double stranded DNA, double stranded RNA, tRNA and mDNA.

10. An apparatus as recited in claim 6, further comprising a second channel communicating with the first channel by way of the nanopore.

11. An apparatus as recited in claim 10, wherein the second channel is orthogonal to the first channel.

12. An apparatus as recited in claim 10, wherein the second channel is below the first channel wall.

13. An apparatus as recited in claim 10, wherein the second channel is adjacent to the first channel wall.

14. An apparatus as recited in claim 10, wherein the second channel is above the first channel wall.

15. An apparatus for threading a biopolymer through a nanopore, comprising:
   (a) a substrate having a channel wall and a nanopore in the channel wall, the channel wall and nanopore being designed for receiving a biopolymer;
   (b) at least one set of electrodes for moving the biopolymer in a first direction past the nanopore; and
   (c) at least one set of electrodes for moving the biopolymer in a second direction through the nanopore after the biopolymer has been moved past the nanopore, wherein the biopolymer comprises a polynucleotide, and
   wherein the biopolymer comprises a leader molecule attached to the biopolymer for threading the biopolymer through the nanopore.

16. An apparatus as recited in claim 15, wherein the leader molecule comprises at least one fluorophore.

17. An apparatus as recited in claim 16, wherein the apparatus is transparent so that light may be used to detect the fluorophore and its position in the first channel.

18. An apparatus as recited in claim 16, wherein the apparatus is transparent so that light may be used to detect the fluorophore and its position in the second channel.

19. A method of threading a biopolymer through a nanopore, comprising:
   (a) moving the biopolymer with a leader molecule past the nanopore in a first direction; and
   (b) threading the biopolymer through the nanopore in a second direction,
   wherein the leader molecule draws the biopolymer through the nanopore under the influence of an electric field.

20. A method of moving a biopolymer having a leader molecule through a nanopore in a substrate, comprising:
   (a) applying a first electric field in a defined direction to move the leader molecule past the nanopore in the substrate until a portion of the biopolymer is adjacent to the nanopore; and
   (b) applying a second electric field in a second direction to move the biopolymer in a second direction through the nanopore;
   wherein the leader molecule draws the biopolymer through the nanopore under the influence of the second electric field.

21. A method as recited in claim 20, wherein a central portion of the leader molecule enters the nanopore before the rest of the leader molecule, so that the leader molecule is drawn into the nanopore in a doubled configuration.

* * * * *

UNITED STATES PATENT AND TRADEMARK OFFICE
CERTIFICATE OF CORRECTION

PATENT NO. : 7,347,921 B2 Page 1 of 1
APPLICATION NO. : 10/622367
DATED : March 25, 2008
INVENTOR(S) : Barth et al.

It is certified that error appears in the above-identified patent and that said Letters Patent is hereby corrected as shown below:

In column 12, line 5, in Claim 1, delete "bipolymer" and insert -- biopolymer --, therefor.

Signed and Sealed this

Seventh Day of October, 2008

JON W. DUDAS
*Director of the United States Patent and Trademark Office*